United States Patent [19]

Louderback

[11] 4,201,694
[45] May 6, 1980

[54] METHOD FOR INCREASING SHELF-LIFE OF A SERUM BILIRUBIN REFERENCE COMPOSITION AND COMPOSITION PRODUCED THEREBY

[75] Inventor: Allan L. Louderback, Temple City, Calif.

[73] Assignee: Beckman Instruments, Inc., Fullerton, Calif.

[21] Appl. No.: 925,484

[22] Filed: Jul. 17, 1978

[51] Int. Cl.$^2$ ............................................. G01N 33/16
[52] U.S. Cl. .................................. 252/408; 23/230 B; 424/2; 424/3
[58] Field of Search ...................... 252/408; 23/230 B; 424/2, 3; 195/103.5 R, 99

[56] References Cited

U.S. PATENT DOCUMENTS

| | | | |
|---|---|---|---|
| 3,873,269 | 3/1975 | Kraffczyk et al. | 252/408 |
| 3,876,375 | 4/1975 | Maurukas | 252/408 |
| 4,121,905 | 10/1978 | Maurukas | 252/408 |

OTHER PUBLICATIONS

Michaëlsson, M., Scand. J.Clin. Lab. Invest., vol. 13, Suppl. 56, pp. 1–80 (1961).
NBS Standard Reference Material 916, "Bilirubin", (1971) Andrews, A. T., et al., Arch. Biochem. Biophys, vol. 141, pp. 538–546 (1970).
Joint Committee Report, "Recommendation on a Uniform Bilirubin Standard", Clin. Chem., vol. 8 No. 4, pp. 405–407 (1961).
Tietz, N. W., Clinical Chemistry, W. B. Saunders Co., Philadelphia, Pa., 2nd Ed., pp. 1035–1040 (1976).
Zebelman, A. M., et al., Clin. Chem., vol. 22, No. 6, pp. 934–935 (1976).
Doumas, B. T., et al., Clin. Chem., vol. 19, No. 9, pp. 984–993 (1973).
Billing, B. H., et al., Biochem. J., vol. 65, pp. 774–784 (1957).
Henry, R. J., "Clinical Chemistry", Hoeber Med. Div., Harper & Row, N. Y., N. Y., pp. 571–617 (1972).

Primary Examiner—Teddy S. Gron
Attorney, Agent, or Firm—Robert J. Steinmeyer; Robert S. Frieman

[57] ABSTRACT

A stable blood serum bilirubin reference composition characterized in that said composition either (1) possesses a pH of from about 8.3 to about 9.5 or (2) further comprises a sulfhydryl compound in an amount sufficient to enhance the stability of the bilirubin or (3) both possesses a pH of from about 8.3 to about 9.5 and further comprises a sulfhydryl compound in an amount to further enhance the stability of the bilirubin.

19 Claims, No Drawings

METHOD FOR INCREASING SHELF-LIFE OF A SERUM BILIRUBIN REFERENCE COMPOSITION AND COMPOSITION PRODUCED THEREBY

BACKGROUND OF THE INVENTION

1. Field of the Invention

This invention relates to a laboratory material and, more particularly, to a stable blood serum bilirubin reference composition.

2. Description of the Prior Art

A concentration of bilirubin of 20 miligram per 100 mililiter (20 mg%) is used as a criteria by physicians for determining at which point one must transfuse a patient so that there is no brain damage. This procedure usually occurs with newborn infants who undergo considerable trauma during the birth process. The patient will either be transfused or blood exchanged on the basis of a bilirubin test.

At present, controls are made by a lyophilization process to stabilize various analytes including bilirubin. These lyophilized controls must be reconstituted by the clinical laboratory before use. The reconstituted controls are only useful as a calibrator for a maximum period of about one day. The reconstituted control slowly breaks down to lower and lower values. However, the clinical laboratory is always using the calibrator's theoretically high value which, unfortunately, can lead to erroneous results.

Prior art bilirubin standards have been reported to deteriorate about 2% per month when stored at $-23°$ C. This deterioration prohibits long storage at this temperature. Bilirubin standards stored at $-16°$ C. for twelve days exhibits a 4% deterioration at the end of this period. At $-70°$ C., bilirubin standards exhibited relatively good stability, deteriorating about 1% in six months. Tietz, *Fundamentals of Clinical Chemistry*, W. B. Saunders Company, Philadelphia, Penn., 2nd Edition (1976), 1035-1043, and Doumas et al., *Clinical Chemistry*, 19 (9):984 (1973), said publications being incorporated herein in toto by reference.

SUMMARY OF THE INVENTION

The instant invention encompasses a blood serum bilirubin reference composition having an improved shelf life. The blood serum bilirubin reference composition is characterized in that the composition either (1) possesses a pH of about 8.3 to about 9.5 or (2) further comprises a sulfhydryl compound in an amount sufficient to enhance the stability of bilirubin or (3) possesses a pH of from about 8.3 to about 9.5 and further comprises a sulfhydryl compound in an amount sufficient to further enhance the stability of bilirubin.

DESCRIPTION OF THE PREFERRED EMBODIMENTS

The improved blood serum reference composition of the instant invention is of the type comprising blood serum having a bilirubin constituent of a known value. In one embodiment of the instant invention, this invention's improved blood serum reference composition is characterized in that the composition possesses a pH of from about 8.3 to about 9.5, preferably, from about 8.3 to about 8.7, and more preferably about 8.5. The pH of the blood serum reference composition of the instant invention is outside the pH range of 7.3 to 7.4 which the prior art taught to be essential for maximum stability for the bilirubin standard. See Tietz, supra.

The pH can be adjusted by any conventional means employed by those skilled in the art, e.g., by the addition of NaOH to the composition.

In a second embodiment of the instant invention, this invention's improved blood serum reference composition is characterized in that the composition further comprises a sulfhydryl compound in an amount sufficient to further enhance the stability of bilirubin.

The normal range of oxidation-reduction (REDOX) potential for plasma is from about $+7$ to about $+40$ millivolts depending upon the freshness of the plasma. It has been discovered that by reducing the REDOX potential of plasma with sulfhydryl compounds, one is able to greatly prolong the shelf life of a bilirubin composition. Although the exact amount of the sulfhydryl compound employed is not critical, one should avoid using too much sulfhydryl compound in order to avoid cross linking the sulfhydryl bonds. The cross-linking of sulfhydryl bonds forms a disulfide bridge (—S—S—) which results in a polymer matrix. This polymer matrix imparts a gel-like consistency to the composition thereby rendering it undesirable for clinical use. This cross linking generally starts to occur at a REDOX potential of about $-300$ millivolts. In a similar fashion, if too little sulfhydryl compound is employed, the bilirubin composition will not be stable. Therefore, sulfhydryl compounds should be employed in an amount sufficient to enhance the stability of bilirubin without imparting undesirable characteristics to the composition, said amount preferably being sufficient to reduce the REDOX potential of the composition to from about $-30$ to about $-300$, more preferably from about $+100$ to about $-200$, and optimally about $-160$, millivolts.

Any of the numerous sulfhydryl compounds known to those skilled in the art can be employed as a reducing agent in the instant invention. For example, the sulfhydryl compound can be selected from a group consisting of dithioerythreitol, dithiothreitol, mercaptoethanol, cysteine, reduced gluthathione, N-acetyl cysteine, mercaptoacetate, as well as mixtures thereof. Preferably the sulfhydryl compound is dithiothreitol.

In a third embodiment of the instant invention, this invention's improved blood serum reference composition is characterized in that the composition possesses the pH set forth above and further comprises a sulfhydryl compound in an amount as described above.

Although any blood serum reference composition of the type comprising blood serum having a bilirubin constituent of a known value can be employed in the present invention, it is preferred to employ a bilirubin reference composition comprising in its non-biological component from about 40 to about 85, more preferably from about 60 to about 80, weight percent water, from about 15 to about 60, more preferably from about 20 to about 40, weight percent of at least one alkylene polyol having from 2-5 carbon atoms, the remainder being bilirubin and, optionally, other natural biological materials selected from a group consisting of blood serum, enzymes, metabolites, electrolytes, and hormones. This matrix is described in detail in U.S. Pat. No. 3,876,375, said publication being incorporated herein in toto by reference.

The stable blood serum bilirubin reference composition of the instant invention can be employed as a blood serum bilirubin reference standard or as a blood serum bilirubin reference control, i.e., the composition can be employed to either calibrate an instrument or can be employed to periodically verify that the instrument is still operating within the tolerances desired. For the above uses, the blood serum bilirubin reference composition of the instant invention can contain known amounts of bilirubin in amounts of from about 0.1 to 40 or about 1 to about 30 or 2 to about 25 milligrams per deciliter.

The following examples are provided for the purpose of further illustration only and are not intended to be limitations on the disclosed invention.

EXAMPLE 1

Bilirubin compositions comprising in their non-biological component about 66⅔ weight percent water, about 33⅓ weight percent ethylene glycol, and about 10 mg/dl bilirubin and possessing a pH of from 6.0 to 10.0 were incubated at 41° C. for 24 hours and then assayed for bilirubin. Table I shows the percent bilirubin remaining after exposure to the elevated temperature.

TABLE I

| pH   | Recovery, % |
|------|-------------|
| 6.0  | 24          |
| 8.0  | 47          |
| 8.3  | 79          |
| 8.5  | 96          |
| 9.0  | 96          |
| 9.5  | 92          |
| 10.0 | 70          |

Table I clearly shows that at a pH optimum of from about 8.3 to about 9.5 the bilirubin compositions of the instant invention display remarkable stability. Although bilirubin is quite stable at pH 10.0, enzymes are rapidly denatured at this pH. Also, antigen-antibody reactions are also adversely affected at this high pH. Therefore, it is not desirable to adjust the pH of the blood serum bilirubin reference composition to a pH above about 9.5.

EXAMPLE 2

Bilirubin compositions comprising in their non-biological component about 66 ⅔ weight percent water, about 33⅓ weight percent ethylene glycol, about 20 mg/dl bilirubin, varying amounts of a sulfhydryl compound, and possessing a pH of about 8.5 were incubated at 41° C. for 72 hours and then assayed for bilirubin. Table II sets forth the percent bilirubin remaining after exposure to the elevated temperature.

TABLE II

| Reducing Agent | Concentration, mg/dl | REDOX Potential, my | Recovery, % |
|----------------|----------------------|---------------------|-------------|
| None           | —                    | +25                 | 71          |
| DTE            | 5                    | −147                | 90          |
| DTE            | 20                   | −185                | 82          |

Table II clearly shows the unexpected enhancement of stability obtained by employing a sulfhydryl compound to lower the REDOX potential of the composition of the instant invention. The lower improvement noted at a DTE content of 20 mg/dl is due to the cross linking of the sulfhydryl bonds at the elevated temperature of the experiment. This elevated temperature is used in the experiment to accelerate the decomposition of the bilirubin composition. Sulfhydryl bond cross-linking does not occur at a 20 mg/dl DTE content at ordinary use temperatures.

Based on this disclosure, many other modifications and ramifications will naturally suggest themselves to those skilled in the art. These are intended to be comprehended as within the scope of this invention.

The embodiments of the invention in which an exclusive property or privileges is claimed are defined as follows:

1. An improved blood serum reference composition of the type comprising blood serum having a bilirubin constituent of known value, characterized in that said composition possesses a pH of from about 8.3 to about 9.5 and further comprising a sulfhydryl compound in an amount sufficient to further enhance the stability of bilirubin.

2. The composition of claim 1 wherein said sulfhydryl compound is present in an amount such that the oxidation-reduction potential of said composition is from about −30 to about −300 millivolts.

3. The composition of claim 2 wherein said sulfhydryl compound is present in an amount such that the oxidation-reduction potential of said standard is from about −100 to about −200 millivolts and wherein said composition possesses a pH of from about 8.3 to about 8.7.

4. The composition of claim 3 wherein said sulfhydryl compound is present in an amount such that the oxidation-reduction potential of said standard is about −160 millivolts and wherein said composition possesses a pH of about 8.5.

5. The composition of claim 4 wherein said sulfhydryl compound is selected from a group consisting of dithioerythreitol, dithiothreitol, mercaptoethanol, cysteine, reduced gluthionine, N-acetyl cysteine, mercaptoacetate, and mixtures thereof.

6. The composition of claim 5 wherein said sulfhydryl compound is dithiothreitol.

7. An improved bilirubin reference composition comprising in its non-biological component from about 40 to about 85 weight percent water, from about 15 to about 60 weight percent of at least one alkylene polyol having from 2 to 5 carbon atoms, the remainder being bilirubin and, optionally, other natural biological materials selected from a group consisting of blood serum, enzymes, metabolites, electrolytes, and hormones, characterized in that said composition possesses a pH of from about 8.3 to about 9.5.

8. The composition of claim 7 further comprising a sulfhydryl compound in an amount sufficient to further enhance the stability of bilirubin.

9. The composition of claim 8 wherein said sulfhydryl compound is present in an amount such that the oxidation-reduction potential of said composition is from about −30 to about −300 millivolts.

10. The composition of claim 9 wherein said sulfhydryl compound is present in an amount such that the oxidation-reduction potential of said standard is from about −100 to about −200 millivolts and wherein said composition possesses a pH of from about 8.3 to about 8.7.

11. The composition of claim 10 wherein said sulfhydryl compound is present in an amount such that the oxidation-reduction potential of said standard is about −160 millivolts and wherein said composition possesses a pH of about 8.5.

12. The composition of claim 11 wherein said sulfhydryl compound is selected from a group consisting of dithioerythreitol, dithiothreitol, mercaptoethanol, cycsteine, reduced glutathione, N-acetyl cysteine, mercaptoacetate, and mixtures thereof.

13. The composition of claim 12 whrein said sulfhydryl compound is dithiothreitol.

14. The composition of claim 8 wherein bilirubin is present in an amount from about 0.1 to about 40 milligrams per deciliter and wherein said composition comprises from about 60 to about 80 weight percent and from about 20 to about 40 weight percent of said alkylene polyol.

15. The composition of claim 14 wherein said bilirubin is present in an amount from about 1 to about 30 milligrams per deciliter.

16. The composition of claim 15 wherein bilirubin is present in an amount from about 2 to about 25 milligrams per deciliter.

17. A method for increasing the shelf-life of a blood serum bilirubin reference composition comprising adding to said composition a sulfhydryl compound in an amount sufficient to enhance the stability of bilirubin and adjusting the pH of said composition to from about 8.3 to about 9.5.

18. An improved blood serum reference composition of the type comprising blood serum having a bilirubin constituent of known value, characterized in that said composition further comprises a sulfhydryl compound in an amount sufficient to enhance the stability of bilirubin.

19. An improved bilirubin reference composition comprising in its non-biological component from about 40 to about 85 weight percent water, from about 15 to about 60 weight percent of at least one alkylene polyol having from 2 to 5 carbon atoms, the remainder being bilirubin and, optionally, other natural biological materials selected from a group consisting of blood serum, enzymes, metabolites, electrolytes, and hormones, characterized in that said composition further comprises a sulfhydryl compound in an amount to enhance the stability of bilirubin.

* * * * *